United States Patent
Takayanagi

(10) Patent No.: US 11,071,492 B2
(45) Date of Patent: Jul. 27, 2021

(54) APPARATUS AND METHOD FOR PROCESSING PHYSIOLOGICAL INFORMATION, AND COMPUTER READABLE MEDIUM

(71) Applicant: NIHON KOHDEN CORPORATION, Tokyo (JP)

(72) Inventor: Tsuneo Takayanagi, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 124 days.

(21) Appl. No.: 16/199,666

(22) Filed: Nov. 26, 2018

(65) Prior Publication Data

US 2019/0159694 A1    May 30, 2019

(30) Foreign Application Priority Data

Nov. 29, 2017 (JP) .............................. JP2017-228680

(51) Int. Cl.
| | |
|---|---|
| *A61B 5/355* | (2021.01) |
| *G16H 50/20* | (2018.01) |
| *A61B 5/00* | (2006.01) |
| *A61B 5/349* | (2021.01) |
| *A61B 5/366* | (2021.01) |

(52) U.S. Cl.
CPC .............. *A61B 5/355* (2021.01); *A61B 5/349* (2021.01); *A61B 5/366* (2021.01); *A61B 5/7267* (2013.01); *A61B 5/7275* (2013.01); *G16H 50/20* (2018.01); *A61B 5/7221* (2013.01); *A61B 5/7282* (2013.01)

(58) Field of Classification Search
None
See application file for complete search history.

(56) References Cited

U.S. PATENT DOCUMENTS

| | | | |
|---|---|---|---|
| 6,493,579 B1 * | 12/2002 | Gilkerson | A61N 1/3925 607/5 |
| 10,342,449 B2 * | 7/2019 | Baumann | A61B 5/742 |
| 2002/0169483 A1 * | 11/2002 | Henry | A61N 1/39622 607/5 |
| 2003/0097153 A1 * | 5/2003 | Bardy | A61B 5/0456 607/5 |
| 2004/0193064 A1 * | 9/2004 | Shusterman | A61B 5/7264 600/504 |
| 2007/0088223 A1 * | 4/2007 | Mann | A61B 5/0452 600/485 |
| 2008/0082013 A1 * | 4/2008 | Xue | A61B 5/0452 600/509 |

(Continued)

OTHER PUBLICATIONS

Hermans, Ben J.M., et al., "The development and validation of an easy to use automatic QT-interval algorithm", ?PLOS ONE 12 (9): e0184352. https://doi.org/10.1371/journal.pone.0184352, Sep. 1, 2017, pp. 1-14, University of Adelaide, Australia.

*Primary Examiner* — Kennedy Schaetzle
(74) *Attorney, Agent, or Firm* — Pearne & Gordon LLP

(57) ABSTRACT

A physiological information processing apparatus includes an acquiring section that acquires physiological information of a subject, a classifying section that classifies the physiological information that is acquired by the acquiring section, and an analyzing section that selects an algorithm from a plurality of algorithms according to a result of the classification performed by the classifying section, and that analyzes the classified physiological information by using the selected algorithm.

7 Claims, 5 Drawing Sheets

(56) References Cited

U.S. PATENT DOCUMENTS

| | | | | |
|---|---|---|---|---|
| 2008/0242968 | A1* | 10/2008 | Claus | G06K 9/20 |
| | | | | 600/407 |
| 2010/0226475 | A1* | 9/2010 | Smith | A61B 6/502 |
| | | | | 378/37 |
| 2010/0246913 | A1* | 9/2010 | Srinivas | G06K 9/4671 |
| | | | | 382/131 |
| 2010/0274146 | A1* | 10/2010 | Li | A61B 5/7264 |
| | | | | 600/515 |
| 2011/0257549 | A1* | 10/2011 | Wysocki | A61M 16/024 |
| | | | | 600/529 |
| 2013/0072806 | A1* | 3/2013 | Zhang | A61B 5/7264 |
| | | | | 600/485 |
| 2013/0274624 | A1* | 10/2013 | Mahajan | A61N 1/3622 |
| | | | | 600/518 |
| 2017/0095214 | A1* | 4/2017 | Ramachandran | A61B 5/0402 |
| 2018/0303354 | A1* | 10/2018 | Li | A61B 5/02416 |
| 2019/0231274 | A1* | 8/2019 | Ghosh | A61B 5/021 |

* cited by examiner

| QT TIME INT. / T-WAVE AMP. | QT SHORTENED | QT NORMAL | QT EXTENDED |
|---|---|---|---|
| LARGE (HIGH) | C1 | C4 | C7 |
| NORMAL | C2 | C5 | C8 |
| SMALL (LOW) | C3 | C6 | C9 |

| CLASS | ALGORITHM |
|---|---|
| C1 | FIRST ALGORITHM |
| C2 | SECOND ALGORITHM |
| C3 | THIRD ALGORITHM |
| C4 | FOURTH ALGORITHM |
| C5 | FIFTH ALGORITHM |
| C6 | SIXTH ALGORITHM |
| C7 | SEVENTH ALGORITHM |
| C8 | EIGHTH ALGORITHM |
| C9 | NINTH ALGORITHM |

APPARATUS AND METHOD FOR PROCESSING PHYSIOLOGICAL INFORMATION, AND COMPUTER READABLE MEDIUM

BACKGROUND

The presently disclosed subject matter relates to a physiological information processing apparatus and a physiological information processing method. The presently disclosed subject matter further relates to a computer readable medium to store a program for causing a computer to execute the physiological information processing method.

Hermans B J M, Vink A S, Bennis F C, Filippini L H, Meijborg V M F, Wilde A A M, et al. (2017) "The development and validation of an easy to use automatic QT-interval algorithm," PLos ONE 12 (9): e0184352, (https://doi.org/10.1371/journal.pone.0184352) (hereinafter referred to as Hermans) discloses a method for analyzing physiological information such as a measured electrocardiogram waveform.

In the case where the end point of the T-wave of a measured electrocardiogram waveform is to be detected, a peak of the T-wave is searched based on the prediction that a peak of the T-wave must be detected within a predetermined range which is in the rear of the QRS wave on the time axis.

In this case, the predetermined range where a peak of the T-wave is searched is set by using usual values using various databases. In the above non-patent literature, Hermans, for example, the range where a peak of the T-wave is searched is an interval between R+50 ms and R+0.7 RR interval.

In an electrocardiogram waveform, however, the amplitude of the electrocardiogram waveform and the time axis interval are sometimes largely deviated from those of a typical electrocardiogram waveform because of various causes such as diseases of the subject and the measurement environment. Even when the T-wave in an electrocardiogram waveform is searched by using usual values, therefore, it often occurs that a peak of the T-wave cannot be found, and the end point of the T-wave cannot be correctly detected.

The present disclosure is to provide a physiological information processing apparatus, physiological information processing method, and program which can accurately analyze physiological information.

SUMMARY

According to an aspect of the invention, a physiological information processing apparatus includes:

an acquiring section that acquires physiological information of a subject;

a classifying section that classifies the physiological information acquired by the acquiring section; and an analyzing section that selects an algorithm from a plurality of algorithms according to a result of the classification performed by the classifying section, and that analyzes the classified physiological information by using the selected algorithm.

According to the configuration, first, the classifying section classifies the physiological information. In accordance with a result of the classification, the analyzing section selects an algorithm to be used, from the plurality of prepared algorithms, and analyzes the classified physiological information by using the selected algorithm. Therefore, the analysis is performed by using an algorithm which is suitable for the classified physiological information, and the physiological information can be accurately analyzed.

According to another aspect of the invention, a physiological information processing method includes:

acquiring physiological information of a subject;

classifying the physiological information acquired from the subject;

selecting an algorithm from a plurality of algorithms in accordance with the classification; and analyzing the classified physiological information by the selected algorithm.

In the method, first, the physiological information is classified. In accordance with a result of the classification, an algorithm to be used is selected from the plurality of prepared algorithms. Then, the classified physiological information is analyzed by using the selected algorithm. According to the method, the physiological information is analyzed more accurately by an algorithm which is suitable for the classification result.

According to another aspect of the invention, a computer readable medium which stores a program causing a computer to execute a process for processing physiological information. The process includes:

acquiring physiological information of a subject;

classifying the physiological information acquired from the subject;

selecting an algorithm from a plurality of algorithms in accordance with the classification; and analyzing the classified physiological information by the selected algorithm.

According to the program, a computer executes an analysis by an algorithm which is suitable for the classification result, and the physiological information is analyzed more accurately.

According to the disclosure, physiological information is accurately analyzed.

DETAILED DESCRIPTION OF EMBODIMENTS

Figure 1:
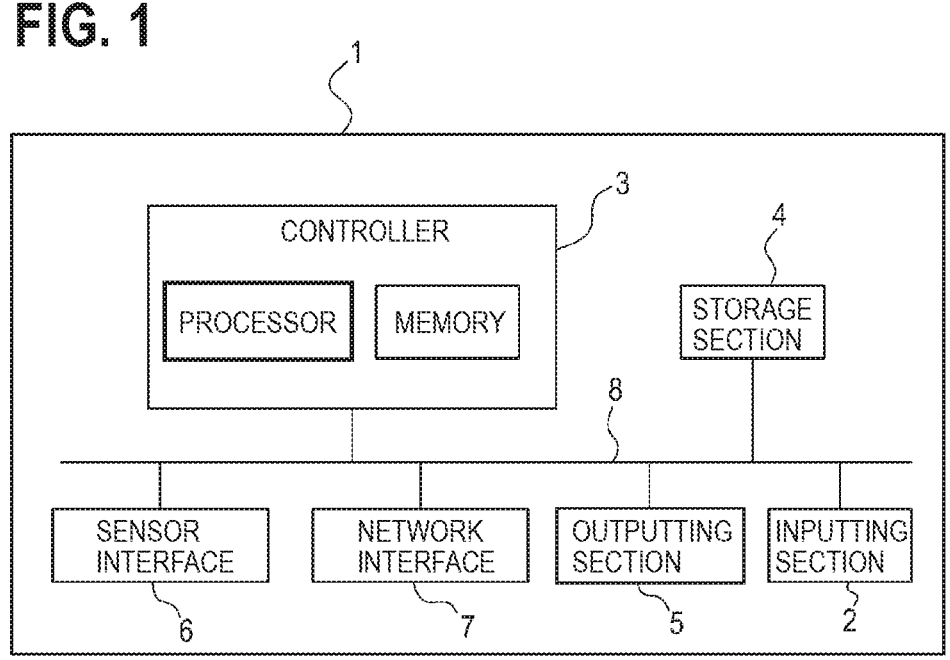
FIG. 1 is a hardware diagram illustrating a physiological information processing apparatus of an embodiment of the disclosure.

Hereinafter, an embodiment will be described with reference to the drawings. FIG. 1 is a hardware diagram illustrating a physiological information processing apparatus 1 (hereinafter, referred to as "processing apparatus 1") of the embodiment.

The processing apparatus 1 can include an inputting section 2, a controller 3, a storage 4, an outputting section 5, a sensor interface 6, and a network interface 7. The inputting section 2, the controller 3, the storage 4, the outputting section 5, the sensor interface 6, and the network interface 7 are electrically connected to one another via a bus 8.

The processing apparatus 1 analyzes physiological information. Physiological information consists of various kinds of information relating to the living body, such as information of physiological waveforms such as an electrocardiogram waveform and the pulse wave, and that of images of a section of a blood vessel, and the heart. The processing apparatus 1 may be a dedicated apparatus for processing physiological information, such as an electrocardiograph, a general-purpose apparatus such as a personal computer, a smart phone, or a tablet, or a wearable device such as Apple Watch (registered trademark).

The inputting section 2 is configured so as to receive an input operation performed by an inspector who operates the processing apparatus 1, and produce an instruction signal corresponding to the input operation. For example, the inputting section 2 is configured by operation buttons which are attached to the housing of the processing apparatus 1, a mouse and keyboard which are connected to the housing, or a touch panel which is placed on the housing. The instruction signal which is produced by the inputting section 2 is supplied to the controller 3 via the bus 8.

The controller 3 is configured so as to perform a control relating to the processing apparatus 1, in accordance with the instruction signal supplied from the inputting section 2. The controller 3 includes one or more processor and one or more memory. The memory is configured so as to store computer readable instructions (programs), and, for example, by a ROM (Read Only Memory) which stores various programs and the like, a RAM (Random Access Memory) having a plurality of work areas in which various programs to be executed by the processor, and the like are stored, etc. For example, the processor is a CPU (Central Processing Unit), an MPU (Micro Processing Unit), and/or a GPU (Graphics Processing Unit), and is configured so as to develop a designated one of the various programs installed in the ROM, in the RAM, and execute various processes in cooperation with the RAM.

The processor may develop a physiological information processing program for causing the processor to execute a physiological information processing method which will be described later, in the RAM, and execute the physiological information processing program in cooperation with the RAM, thereby enabling the controller 3 to control various operations of the processing apparatus 1. The controller 3 and the physiological information processing program will be described in detail later.

For example, the storage 4 is a storage device such as an HDD (Hard Disk Drive), an SSD (Solid State Drive), or a USB flash memory, and configured so as to store programs and various data. The programs stored in the storage 4 are the physiological information processing program, a plurality of algorithms which are to be used in analysis, and the like. The various data stored in the storage 4 are data relating to physiological information, and the like. The data relating to physiological information are waveform data indicating a plurality of electrocardiogram waveforms (an example of the physiological waveform) which continuously appear on the time axis, and the like. The waveform data may be acquired by an electrocardiogram sensor which is not illustrated, in real time (simultaneously with measurement), and then stored in the storage 4 via the sensor interface 6. The waveform data may be measurement result data (past measurement results) which have been already measured. In the case of measurement result data which have been already measured, the data may be acquired in the storage 4 via the network interface 7, or acquired through an external device such as a USB memory.

The outputting section 5 is configured by a device which outputs analysis results of the processing apparatus 1. For example, the outputting section 5 is a displaying device such as a liquid crystal display or an organic EL display, a printing device such as an inkjet printer or a laser printer, or the like.

The sensor interface 6 is an interface for connecting the sensor which is not illustrated, to the processing apparatus 1.

The network interface 7 is configured so as to connect the processing apparatus 1 to a communication network.

The processing apparatus 1 and the sensor interface 6 or the network interface 7 may be connected to each other through a wired connection or a wireless connection.

Figure 2:
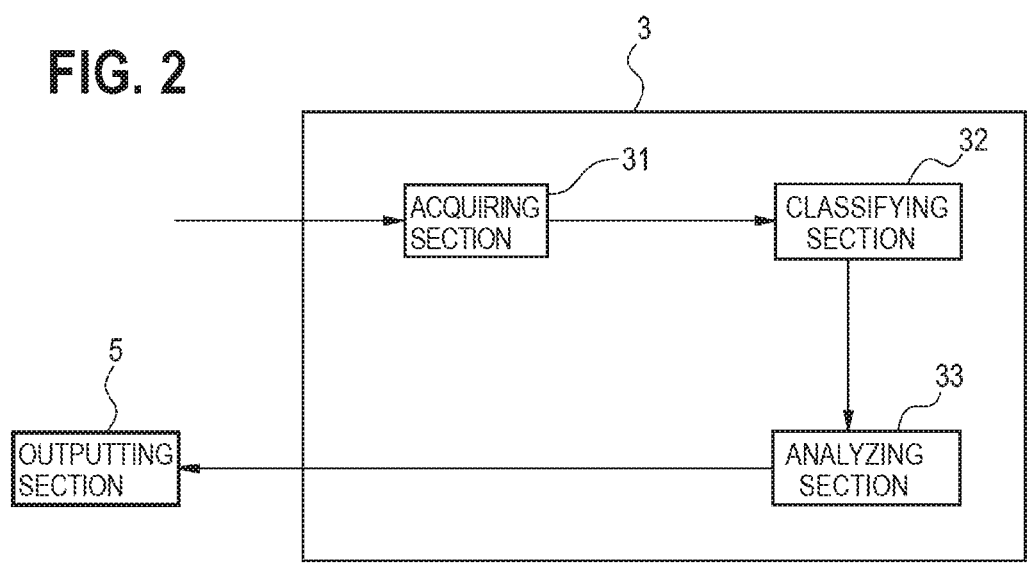
FIG. 2 is a functional block diagram of a controller.

As illustrated in FIG. 2, the controller 3 includes an acquiring section 31, a classifying section 32, and an analyzing section 33.

Figures 3, 4:
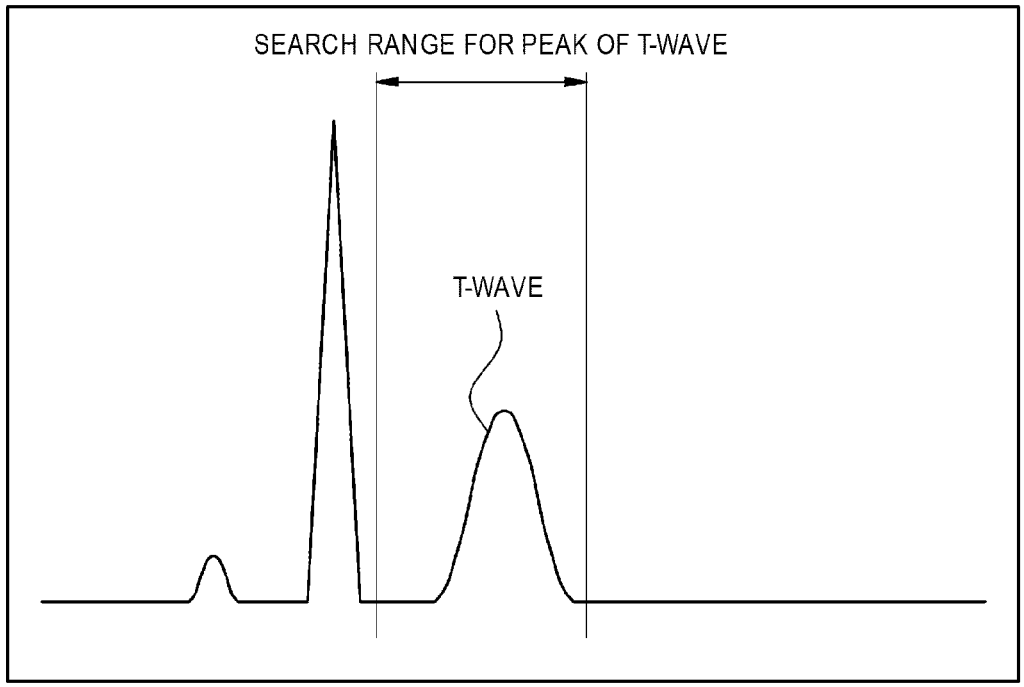
FIG. 3 diagrammatically illustrates analysis of a physiological waveform.
FIG. 4 illustrates an example of a classification table.

The acquiring section 31 is configured so as to acquire physiological information of the subject from the sensor interface 6, the network interface 7, or the storage 4. FIG. 3 diagrammatically illustrates analysis of a physiological waveform, and shows an electrocardiogram waveform (an example of the physiological waveform) containing the QRS wave and T-wave which are acquired by the acquiring section 31.

The physiological information which is acquired by the acquiring section 31 is supplied to the classifying section 32.

The classifying section 32 is configured so as to classify the physiological information acquired by the acquiring section 31. The classifying section 32 classifies the physiological information based on an approximate feature seen in a physiological waveform or the like.

FIG. 4 illustrates an example of a classification table which is used in the classification performed by the classifying section 32. As illustrated in FIG. 4, the classifying section 32 classifies a physiological waveform into classification results C1 to C9 based on the differences in the QT time interval (an example of a time interval on the time axis) and the amplitude (height) of the T-wave in an electrocardiogram waveform. With respect to the classification criteria used in the classification table, for example, the QT time interval may be classified so that a time interval of 350 ms or shorter is classified as "the QT time interval is shortened (hereinafter, referred to as "QT shortened")," a time interval of 450 ms or longer is classified as "the QT time interval is extended (hereinafter, referred to as "QT extended")," and a time interval of longer than 350 ms and shorter than 450 ms is classified as "the QT time interval is normal (hereinafter, referred to as "QT normal")".

For example, the classifying section 32 may be constructed based on learning in which physiological information is previously subjected to deep learning by using a neural network.

The classification result of the classifying section 32 is output from the classifying section 32 to the analyzing section 33.

The analyzing section 33 is configured so as to select an algorithm to be used, from a plurality of prepared algorithms according to the classification result of the classifying section 32, and analyze classified physiological information by the selected algorithm. Each of the plurality of prepared algorithms is constructed so as to be able to perform the optimum analysis coincident with the classification which is based on the approximate feature used in the classifying section 32.

Figures 5, 6:
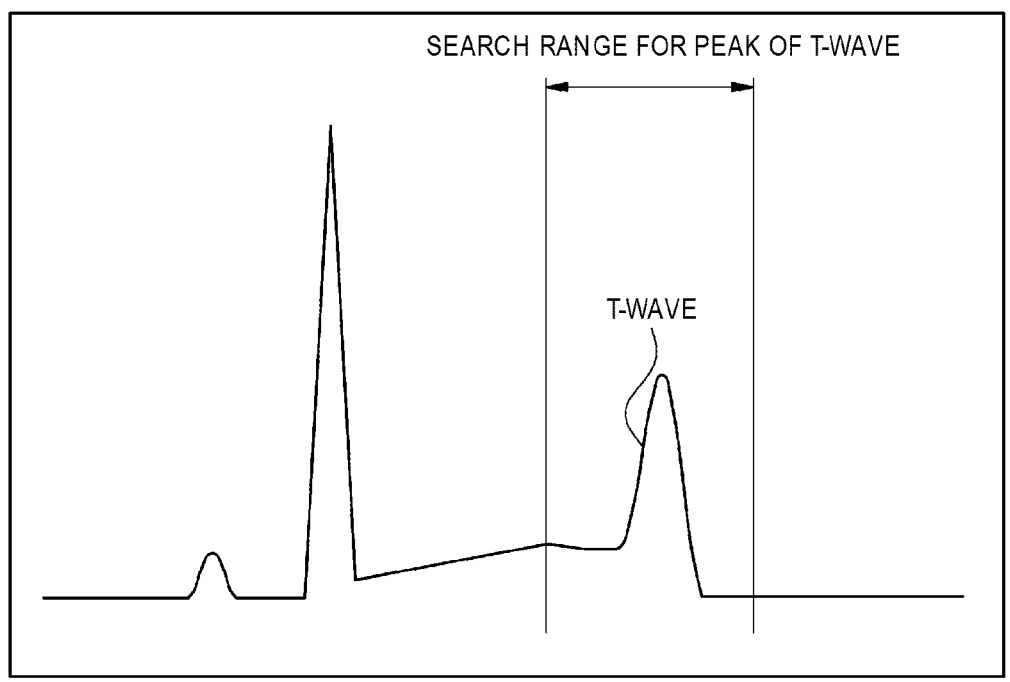
FIG. 5 illustrates an example of a plurality of algorithms.
FIG. 6 diagrammatically illustrates analysis of a physiological waveform.

Examples of the plurality of algorithms to be used in analysis are first to ninth algorithms illustrated in FIG. 5. In this case, the analyzing section 33 is configured so as to select an algorithm according to the classification results C1 to C9 that are acquired from the classifying section 32, from a plurality of first to ninth algorithms which are prepared. The analyzing section 33 analyzes an electrocardiogram waveform corresponding to the classification result, by using the selected algorithm. The electrocardiogram waveform corresponding to the classification result may be supplied from the acquiring section 31 to the analyzing section 33, or from the storage 4 to the analyzing section 33.

Figure 7:
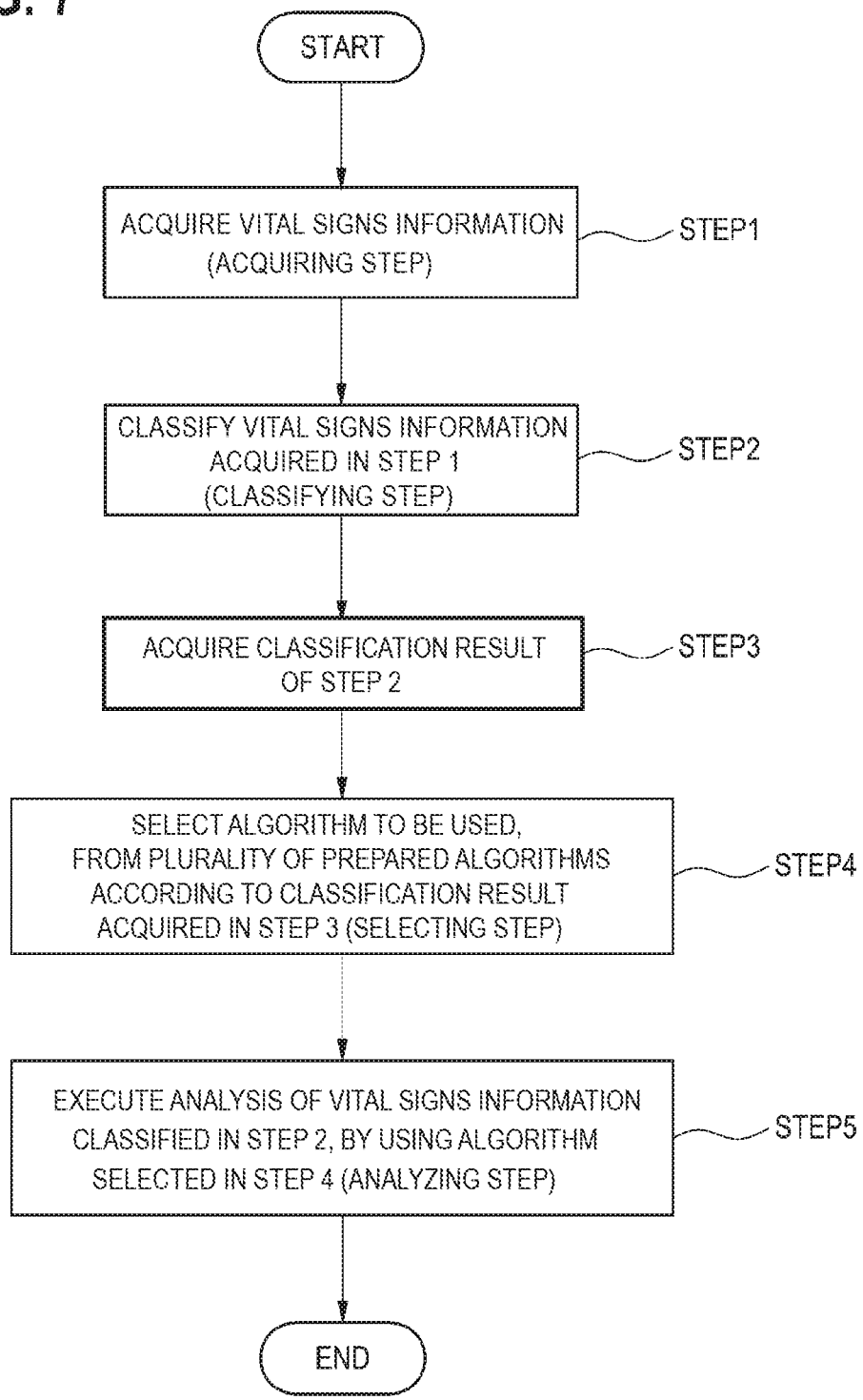
FIG. 7 is a flowchart illustrating an example of a physiological information processing method of the embodiment.

Next, a processing method in the processing apparatus 1 will be described with reference to FIGS. 3 to 7. FIG. 7 is a flowchart illustrating an example of a physiological information processing method (hereinafter, referred to as "processing method") of the embodiment.

As illustrated in FIG. 7, the acquiring section 31 of the processing apparatus 1 acquires in STEP 1 physiological information which is acquired from the subject (the acquiring step). In the embodiment, a case where the acquiring section 31 acquires the physiological waveform illustrated in FIG. 3 or 6 will be described. The acquiring section 31 A/D converts the acquired physiological waveform to digital data (waveform data), and supplies the waveform data to the classifying section 32.

In STEP 2, the classifying section 32 classifies the waveform data which are acquired in STEP 1 (the classifying step). In the case where waveform data relating to FIG. 3 are acquired, the classifying section 32 classifies the waveform data into "QT shortened" and "amplitude of T-wave is normal (normal)" (classification result C2) (FIG. 4). In the case where waveform data relating to FIG. 6 are acquired, the classifying section 32 classifies the waveform data into "QT extended" and "amplitude of T-wave is normal (normal)" (classification result C8) (FIG. 4).

The classifying section 32 outputs the classification result to the analyzing section 33.

In STEP 3, the analyzing section 33 acquires the classification result in STEP 2 from the classifying section 32. In STEP 4, the analyzing section 33 selects an algorithm which is suitable for the classification result, from the plurality of prepared algorithms (the first to ninth algorithms) according to the classification result acquired in STEP 3 (the selecting step). In the case where the acquired classification result is the classification result C2, the analyzing section 33 selects the second algorithm as the algorithm which is suitable for the classification result C2. In the case where the acquired classification result is the classification result C8, the analyzing section 33 selects the eighth algorithm as the algorithm which is suitable for the classification result C8.

In STEP 5, the analyzing section 33 executes analysis of the waveform data which are classified in STEP 2, by using the algorithm (the second algorithm or the eighth algorithm) that is selected in STEP 4 (the analyzing step). The result of the analysis in the analyzing section 33 may be output from the outputting section 5, or stored in the storage 4.

As described above, according to the processing apparatus 1 of the embodiment, physiological information is first classified by the classifying section 32 (STEP 2 in FIG. 7). In accordance with the classification result (one of the classification result C1 to C9), the analyzing section 33 selects the algorithm to be used, from the plurality of prepared algorithms (the first to ninth algorithms) (STEP 4 in FIG. 7). The classified physiological information is analyzed by using the selected algorithm (STEP 5 in FIG. 7). As a result, the analysis is performed by the algorithm which is suitable for the classified physiological information, and the physiological information is analyzed accurately.

Figure 8:
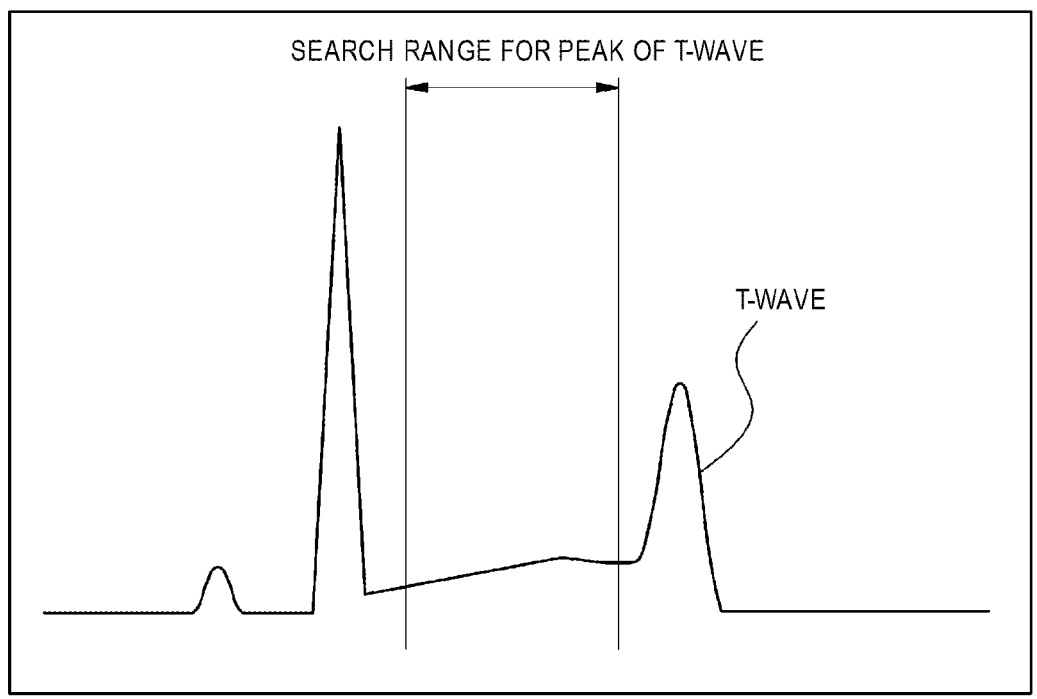
FIG. 8 diagrammatically illustrates analysis of a physiological waveform in the prior art.

In the analysis of an electrocardiogram waveform, in the case where a usual value is used, for example, in the detection of a peak of the T-wave, conventionally, there is a case where, with respect to a waveform which is deviated from a standard waveform, a peak of the T-wave cannot be detected. FIG. 8 illustrates a standard range where a peak of the T-wave is searched for. In the example illustrated in FIG. 8, the T-wave is deviated from the search range for a peak of the T-wave, and a peak of the T-wave cannot be detected. In this case, also the QT time interval cannot be detected.

In the above-described processing apparatus 1 of the embodiment, by contrast, physiological information is classified by the classifying section 32. In accordance with the result of the classification, the algorithm to be used is selected by the analyzing section 33, and the analysis is performed by using the selected algorithm. Therefore, physiological information which cannot be correctly analyzed in the prior art, such as the QT shortened (FIG. 3) and the QT extended (FIG. 6) can be accurately analyzed.

Moreover, physiological information is classified by the classifying section 32 which is constructed based on learning in which physiological information is previously subjected to deep learning by using a neural network. Therefore, accurate classification is performed without relying on the subjective view of the inspector (a feature value which is set by the inspector).

Moreover, physiological information contains physiological waveforms, and the classifying section 32 is configured so as to perform classification based on time intervals in the physiological waveform. Therefore, a physiological waveform is classified more appropriately.

In order to realize the processing apparatus 1 of the embodiment by using software, the physiological information processing program may be pre-installed in the memory (the storage section such as a ROM) of the controller 3. Alternatively, the physiological information processing program may be stored on a computer readable storage medium such as a magnetic disk (an HDD or a floppy disk), an optical disk (a CD-ROM, a DVD-ROM, a Blu-ray (registered trademark) disk, or the like), a magneto-optical disk (an MO or the like), or a flash memory (an SD card, a USB memory, an SSD, or the like). In the alternative, when the physiological information measurement program which is stored in a storage medium is read by a disk drive or the like disposed in the processing apparatus 1, the physiological information measurement program is installed in the memory. Then, the program which is installed in the memory is loaded into the RAM, and the processor executes the program which is loaded into the RAM.

Alternatively, the physiological information processing program may be downloaded from a computer on a communication network, through the network interface 7. Also in the alternative, same or similarly, the downloaded program is installed in the memory.

The disclosure is not limited to the above-described embodiment and modifications, and may be adequately subjected to modifications, improvements, and the like. In addition, the materials, shapes, forms, numbers, places, and the like of the components of the above-described embodiment are arbitrary and not limited insofar as the disclosure is achieved.

Although, in the above, the embodiment in which a physiological waveform is classified based on the differences in the QT time interval and the amplitude of the T-wave has been described, the classification indexes in the embodiment are not limited to the QT time interval and the T-wave. For example, the processing apparatus 1 and processing method of the disclosure can be used also in classification of a physiological waveform which is based on the PR interval.

In the case where an electrocardiogram waveform (an example of the physiological waveform) is classified based on the PR interval, the classifying section 32 classifies an acquired electrocardiogram waveform (A/D converted waveform data) based on the PR interval, and classification is performed so that a case where the PR interval is shortened is classified as C11, that where the PR interval is normal is classified as C12, and that where the PR interval is extended is classified as C13. In this case, the analyzing section 33 selects an algorithm according to the corresponding one of the classification results C11 to C13, from eleventh to thirteenth algorithms which are prepared, and analyzes the electrocardiogram waveform by using the selected algorithm. For example, the eleventh algorithm can be set to an algorithm relating to the WPW syndrome, and is selected in the case of the classification result C11. For example, the thirteenth algorithm can be set to an algorithm relating to the first-degree atrioventricular block, and is selected in the case of the classification result C13.

The processing apparatus 1 and the processing method can be used also in the case where physiological information is an image. An example in which, in calculation of the ventricular cavity area, an image acquired by the ultrasonic echo is used will be described.

The classifying section 32 acquires an image of a region including the heart from the acquiring section 31, and classifies an approximate position of the heart in the image, by performing deep learning on the image. In the classification, the classifying section 32 divides the whole image to be classified, into a plurality of regions (for example, nine regions), and the divisions are set as classification results C21 to C29. In the acquired image, for example, the classifying section 32 classifies an approximate position where the heart is located, as the classification result C28.

The analyzing section 33 selects an algorithm according to the classification result C28 from twenty-first to twenty-ninth algorithms which are prepared, and performs analysis of the image by using the selected algorithm. For example, the twenty-eighth algorithm can be set as an algorithm for calculating the area of the inside of the heart. The analyzing section 33 selects the twenty-eighth algorithm in accordance with the classification result C28, detects the inner wall of the heart by using the selected twenty-eighth algorithm, and calculates the inside area of the heart.

Although, in the above, the example in which the number OF prepared algorithms, and that of the kinds of classification results are equal to each other has been described, the numbers may be different from each other. For example, the number of the kinds of classification results may be smaller than that of prepared algorithms.

The configuration of the processing apparatus is not limited to that where the plurality of algorithms to be used in analysis are stored in the storage 4. The plurality of algorithms to be used in analysis may be stored in the controller 3. The plurality of algorithms to be used in analysis may be stored in an external device such as a USB memory. The plurality of algorithms which are stored in the external device may be acquired by the analyzing section 33 via the network interface 7.

Although the processing apparatus 1 includes the outputting section 5, the processing apparatus 1 of the disclosure is not limited to the above-described configuration. The outputting section 5 may be disposed outside the processing apparatus 1. In the case where the outputting section 5 is disposed outside the processing apparatus 1, the processing apparatus 1 may transmit information relating to classification and analysis to the outputting section 5 via the network interface 7, or the outputting section 5 may acquire the information via a storage medium such as a USB memory.

What is claimed is:

1. A physiological information processing apparatus comprising:
    an acquiring section that is configured to acquire an electrocardiogram waveform of a subject;
    a classifying section that is configured to classify the electrocardiogram waveform acquired by the acquiring section; and
    an analyzing section that is configured to select an algorithm from a plurality of algorithms according to a result of the classification performed by the classifying section, and that is configured to analyze the classified electrocardiogram waveform by using the selected algorithm, wherein:
    the classifying section is configured to perform classification based on a time interval in the electrocardiogram waveform,
    the analysis of the classified electrocardiogram waveform comprises detecting a peak of a T-wave in the classified electrocardiogram waveform, and
    the analyzing section is configured to select the algorithm so that the detected peak of the T-wave is within a search range of the selected algorithm.

2. The physiological information processing apparatus according to claim 1, wherein the classifying section is a machine learning system trained with an electrocardiogram waveform subjected to deep learning by using a neural network.

3. The physiological information processing apparatus according to claim 1, wherein the classifying section is configured to classify the electrocardiogram waveform based on a time and an amplitude of the waveform.

4. The physiological information processing apparatus according to claim 3,
    wherein the classifying section is configured to classify the electrocardiogram waveform into at least three categories related to the time, and
    wherein the classifying section is configured to classify the electrocardiogram waveform into at least three categories related to the amplitude.

5. The physiological information processing apparatus according to claim 1, wherein the time interval is a Q-T time interval.

6. A physiological information processing method comprising:
    acquiring an electrocardiogram waveform of a subject;
    classifying the electrocardiogram waveform acquired from the subject;
    selecting an algorithm from a plurality of algorithms in accordance with the classification; and
    analyzing the classified electrocardiogram waveform by the selected algorithm, wherein:
    the classifying is based on a time interval in the physiological waveform,
    analyzing the classified electrocardiogram waveform comprises detecting a peak of a T-wave in the classified electrocardiogram waveform, and
    the algorithm is selected so that the detected peak of the T-wave is within a search range of the selected algorithm.

7. A computer readable medium which stores a program causing a computer to execute a process for processing physiological information, the process comprising:
- acquiring an electrocardiogram waveform of a subject;
- classifying the electrocardiogram waveform acquired from the subject;
- selecting an algorithm from a plurality of algorithms in accordance with the classification; and
- analyzing the classified electrocardiogram waveform by the selected algorithm, wherein:
- the classifying is based on a time interval in the physiological waveform,
- analyzing the classified electrocardiogram waveform comprises detecting a peak of a T-wave in the classified electrocardiogram waveform, and
- the algorithm is selected so that the detected peak of the T-wave is within a search range of the selected algorithm.

\* \* \* \* \*